United States Patent [19]

Tsukada et al.

[11] Patent Number: 5,665,574
[45] Date of Patent: *Sep. 9, 1997

[54] METHOD FOR PREPARING N-ACETYLNEURAMINIC ACID

[75] Inventors: Yoji Tsukada, Kyoto; Yasuhiro Ohta, Uji, both of Japan

[73] Assignee: Marukin Shoyu Co., Ltd., Japan

[*] Notice: The term of this patent shall not extend beyond the expiration date of Pat. No. 5,472,860.

[21] Appl. No.: 528,120

[22] Filed: Sep. 14, 1995

Related U.S. Application Data

[63] Continuation of Ser. No. 122,555, filed as PCT/JP92/00757 Sep. 12, 1992, Pat. No. 5,472,860.

[30] Foreign Application Priority Data

Feb. 3, 1992 [JP] Japan .................... 4-17206

[51] Int. Cl.$^6$ ............... C12P 19/02; C12P 19/06; C07H 3/02; C12N 9/08
[52] U.S. Cl. ............... 435/105; 435/84; 435/232; 536/18.7; 536/55.2; 536/125
[58] Field of Search ............... 435/105, 84, 232; 536/18.7, 55.2, 125

[56] References Cited

U.S. PATENT DOCUMENTS

| | | | |
|---|---|---|---|
| 5,071,750 | 12/1991 | Kragl et al. | 435/94 |
| 5,162,513 | 11/1992 | Wong | 536/1.1 |

OTHER PUBLICATIONS

Ethan S. Simon et al., J. Am. Chem. Soc. 1988, 110, 7159–7163; "Synthesis of CMP–NeuAc from N–Acetylglucosamine: Generation of CTP from CMP using Adenylate Kinase$^{1,2}$".

Mahn–Joo Kim et al., J. Am. Chem. Soc. 1988, 110, 6481–6486; "Enzymes in Carbohydrate Synthesis: N–Acetylneuraminic Acid Aldolase Catalyzed Reactions and Preparation of N–Acetyl–2–deoxy–D–neuraminic Acid Derivatives".

Udo Kragl et al., Angen. Chem. Int. Engl., 30 (1991) No. 7; "Enzymatic Two–Step Synthesis of N–Acetylneuraminic Acid in the Enzyme Membrane Reactor".

Tomoaki Tanase et al., J. Chem. Soc., Chem. Commun., 1986, 1001–1003; "Novel C–2 Epimerization of Aldoses and Stereoselective Uptake of One of the Epimeric Aldoses by Nickel(II) Complexes".

Norman E. Good et al., Biochemistry, vol. 5, No. 2, 467–477, 1966; "Hydrogen Ion Buffers for Biological Research".

Toshiaki Imamura et al., Kagaku-no-ryoiki 30–2, 79–87; "Good's Buffer Development and Progress of New pH Buffers" (1976).

Primary Examiner—Michael G. Wityshyn
Assistant Examiner—Francisco C. Prats
Attorney, Agent, or Firm—Knobbe Martens Olson & Bear, LLP

[57] ABSTRACT

A method for preparing N-acetylneuraminic acid characterized in reacting N-acetylglucosamine with pyruvic acid in an alkaline condition by the action of N-acetylneuraminic acid lyase.

13 Claims, No Drawings

METHOD FOR PREPARING N-ACETYLNEURAMINIC ACID

This is a continuation of application Ser. No. 08/122,555, filed Sep. 30, 1993, now U.S. Pat. No. 5,472,860, which is a 371 of PCT/JP92/00757, filed Sep. 12, 1992.

FIELD OF THE INVENTION

The present invention relates to a method for preparing N-acetylneuraminic acid.

DISCLOSURE OF THE INVENTION

N-acetylneuraminic acid is an important substance in that it is a most ubiquitous substance in sialic acids, widely distributed in organs, body fluids and secreted fluid of the living body and that the relation of N-acetylneuraminic acid to hemagglutination, inter-cellular recognition, metabolism of serum proteins and the like are known.

N-acetylneuraminic acid, such an important substance, is hitherto prepared by hydrolysis of capsular polysaccharide of *E. coli* and also produced by hydrolysis of natural material, such as a nest of petrel, an egg, milk and the like.

The method of using natural material as a raw material has problems in that it is difficult to prepare a large quantity of N-acetylneuraminic acid whose demand is increasing yearly due to the limitation of absolute amount of raw material; separation and purification of N-acetylneuraminic acid from other contaminants after hydrolyzing natural material is not easy; and that preparation cost of the acid is high. An inexpensive mass production technique of N-acetylneuraminic acid is not fully developed.

To solve the problems, synthetic methods using an enzyme have been variously examined.

For example, Kim et al. [*J. Am. Chem. Soc.*, 110, 6481–6486 (1988)] reported a method for preparing N-acetylneuraminic acid by reacting N-acetylmannosamine with pyruvic acid in the presence of N-acetylneuraminic acid lyase. However, this method is not practical in that the method uses N-acetylmannosamine as a starting material which is expensive and difficult to procure in a large quantity.

N-acetylmannosamine can be prepared by isomerizing N-acetylglucosamine in a strong alkaline condition, i.e., pH about 12 [*Simon et al., J. Am. Chem. Soc.*, 110, 7159–7163 (1988)]. However, in this method the proportion of N-acetylglucosamine and N-acetylmannosamine is N-acetylglucosamine: N-acetylmannosamine=3:1 in an equilibrium state so that the separating operation of N-acetylmannosamine is not easy because of a low proportion of N-acetylmannosamine.

A method for preparing N-acetylneuraminic acid by reacting N-acetylglucosamine with pyruvic acid in the presence of N-acetylneuraminic acid lyase and epimerase is also proposed [e.g., Kragl et al, *Angew. Chem. Int. Ed. Eng.*, 30, 827–828 (1991)]. In this method, N-acetylglucosamine is converted into N-acetylmannosamine successively, and then N-acetylmannosamine is converted to N-acetylneuraminic acid by the action of N-acetylneuraminic acid lyase. However, acquisition of epimerase isomerizing N-acetylglucosamine is difficult, and also the conversion ratio from N-acetylglucosamine to N-acetylneuraminic acid is as low as 28%. This method is not practical either.

It is an object of the present invention to provide a simple and practical method for preparing N-acetylneuraminic acid.

The inventor has conducted extensive research to accomplish the object and found that reacting N-acetylglucosamine with pyruvic acid in the presence of N-acetylneuraminic acid lyase in an alkaline condition, that is, high pH region, which is not used hitherto so as to avoid denaturation of the enzyme and due to departing from optimum pH of N-acetylneuraminic acid lyase, converts N-acetylglucosamine into N-acetylneuraminic acid effectively under a repression of enzyme denaturation because of the protecting effect of starting materials, i.e., N-acetylglucosamine and pyruvic acid.

Thus, the present invention provides a method for preparing N-acetylneuraminic acid characterized in reacting N-acetylglucosamine with pyruvic acid in an alkaline condition by the action of N-acetylneuraminic acid lyase.

As used herein, "alkaline condition" means that the PH value of the reaction mixture is in the range of about 8 to about 12, preferably about 9 to about 12, more preferably about 10 to about 12, and most preferably about 10 to about 11. When the pH value of the reaction mixture is too low, the reaction does not proceed because the conversion from N-acetylglucosamine to N-acetylmannosamine hardly or never occurs. On the other hand, when the PH value of the reaction mixture is too high, the reaction yield decreases due to denaturation of N-acetylneuraminic acid lyase. Reaction temperature is in the range of about 10° C. to about 80° C., preferably about 20° C. to about 50° C., and reaction time is in the range of about 30 minutes to about 240 hours, preferably about 20 hours to about 120 hours. The reaction is conducted on standing or in a stirred condition.

The concentrations of each component are as follows:

(1) The quantity of N-acetylglucosamine used, which is not specifically limited, is preferably used in a concentration in the range of about 1 to about 20 W/V %, more preferably about 10 to about 20 W/V %. N-acetylglucosamine can be used in a concentration of up to saturated solubility.

(2) The quantity of pyruvic acid used is, which is not specifically limited, is preferably used in a concentration in the range of about 1 to about 20 W/V %, more preferably about 10 to about 20 W/V %. Pyruvic acid can be used in a concentration of up to saturated solubility.

(3) The quantity of N-acetylneuraminic acid lyase used, which is not specifically limited, can be selected from a wide range of concentration in accordance with an amount of substrates, and is preferably at least 0.01 U, more preferably about 0.1 to about 100 U, and most preferably about 1 to about 50 U per 1 ml of the reaction mixture.

When the concentrations of substrates, i.e., N-acetylglucosamine and pyruvic acid are too low, the total quantity of N-acetylneuraminic acid produced decreases. On the other hand, when the concentrations of substrates, i.e., N-acetylglucosamine and pyruvic acid are too high, purification of N-acetylneuraminic acid becomes harder due to decrease of a proportion of N-acetylneuraminic acid.

When the quantity of N-acetylneuraminic acid lyase used is too low, the reaction requires a longer period of time. On the other hand, when the quantity of N-acetylneuraminic acid lyase used is too high, it is economically wasteful because excessive N-acetylneuraminic acid lyase does not decrease reaction time and does not increase yield.

The pH value of the reaction solution can be adjusted by adding basic substances such as sodium hydroxide, potassium hydroxide, lithium hydroxide and like alkali metal hydroxides, calcium hydroxide, magnesium hydroxide and like alkaline earth metal hydroxides, sodium carbonate, potassium carbonate, sodium bicarbonate, potassium bicarbonate and like alkali metal carbonates or bicarbonates and ammonia and the like in a needed amount to adjust the solution to a desired pH, or using alkaline buffer such as phosphate buffer, Tris-hydrochloric acid buffer, borate buffer, veronal-hydrochloric acid buffer, Good's buffer, diethanolamine-hydrochloric acid buffer and the like.

N-acetylglucosamine can be used in the form of free base or salts thereof, such as hydrochloride, sulfate and the like.

Pyruvic acid can be used in the form of free acid or salts thereof, such as sodium salt, potassium salt, and the like.

N-acetylneuraminic acid lyase derived from both animal and plant kingdoms can be used, and its enzymatic activity is not very affected by purity of N-acetylneuraminic acid lyase.

N-acetylneuraminic acid produced by the method of the invention can be easily isolated from the reaction mixture by using known means. For example, the crystal form of N-acetylneuraminic acid can, be obtained from an organic solvent after purification by ion-exchange column chromatography.

The method of the present invention has the following excellent effects, because the reaction can be conducted in an alkaline condition, in which it has been considered that enzyme is denaturated hitherto, in favor of enzyme-protecting activity of substrates.

(1) The reaction for producing N-acetylneuraminic acid can be conducted using a high concentration of N-acetylglucosamine which is cheap and readily available so that mass production of N-acetylneuraminic acid becomes possible.

(2) The method is a one-pot reaction so that the production step can be simplified.

(3) Epimerase becomes unnecessary, because N-acetylglucosamine is isomerized to N-acetylmannosamine in an alkaline condition.

(4) Under appropriate conditions as to pH of the reaction mixture, quantity of enzyme, substrate concentration and the like, N-acetylneuraminic acid can be produced in a high yield, i.e., 50% or more in a molar ratio to N-acetylglucosamine.

EXAMPLES

The present invention will be described in greater detail using examples and comparative examples. However, the invention is not limited to these examples.

Example 1

* Production of N-acetylneuraminic acid 18 g of N-acetylglucosamine and 18 g of pyruvic acid were dissolved in water. After adjusting the pH value of the solution to 10.5, followed by adding 2000 U of N-acetylneuraminic acid lyase and adjusting the total volume of the solution to 100 ml, the resulting solution was reacted at 30° C. for 48 hours. Determination of N-acetylneuraminic acid by HPLC indicated that the quantity thereof in a reaction mixture was 13 g, and a conversion rate of N-acetylglucosamine used to N-acetylneuraminic acid was about 51%.

The reaction product was isolated on ion-exchange column chromatography using Dowex 1 (registered trademark, product of DOW CHEMICAL CO.) and the eluates were concentrated. The concentrate was treated according to a conventional method to give 10 g of needle crystals of N-acetylneuraminic acid.

Example 2

100 g of N-acetylglucosamine and 200 g of pyruvic acid were dissolved in 100 mM of phosphate buffer (pH 10.0). After adding 15000 U Of N-acetylneuraminic acid lyase and adjusting the total volume of the solution to 1 L, the resulting solution was reacted at 35° C. for 120 hours. The quantity of N-acetylneuraminic acid in a reaction mixture was 56 g, and a conversion rate of N-acetylglucosamine used was about 40%.

The reaction product was isolated on ion-exchange column chromatography using Dowex 1 (registered trademark, product of DOW CHEMICAL CO.) and the eluates were concentrated. The concentrate was treated according to a conventional method to give 42 g of needle crystals of N-acetylneuraminic acid.

Examples 3 to 23 and Comparative Example 1

The reactions were conducted in the same conditions as in example 2 except for alteration of concentrations of N-acetylglucosamine and pyruvic acid, a concentration of N-acetylneuraminic acid lyase, reaction time and pH of phosphate buffer respectively.

The results are demonstrated in table 1 and table 2 as shown below.

TABLE 1

| | | substrate concentration (g/100 ml) | | concentration of NANA (mg/ml) | |
|---|---|---|---|---|---|
| | pH | GlcNAc | Pyr-Na | after 1 day reaction | after 5 day reaction |
| Example | | | | | |
| 3 | 8.0 | 18 | 18 | 0 | 1 |
| 4 | 9.0 | 18 | 18 | 1 | 3 |
| 5 | 9.5 | 18 | 18 | 2 | 7 |
| 6 | 10.0 | 18 | 18 | 19 | 50 |
| 7 | 10.5 | 18 | 18 | 55 | 130 |
| 8 | 11.0 | 18 | 18 | 30 | 60 |
| 9 | 9.0 | 4.5 | 4.5 | 0 | 1 |
| 10 | 9.5 | 4.5 | 4.5 | 1 | 2 |
| 11 | 10.0 | 4.5 | 4.5 | 4 | 11 |
| 12 | 10.5 | 4.5 | 4.5 | 9 | 20 |
| 13 | 11.0 | 4.5 | 4.5 | 2 | 3 |
| Comparative Example | | | | | |
| 1 | 7.5 | 18 | 18 | 0 | 0 |

*concentration of N-acetylneuraminic acid lyase: 10 U/ml

TABLE 2

| | | substrate concentration (g/100 ml) | | concentration of NANA (mg/ml) | |
|---|---|---|---|---|---|
| Example | pH | GlcNAc | Pyr-Na | after 1 day reaction | after 5 day reaction |
| 14 | 9.0 | 18 | 18 | 0 | 1 |
| 15 | 9.5 | 18 | 18 | 1 | 3 |
| 16 | 10.0 | 18 | 18 | 2 | 15 |
| 17 | 10.5 | 18 | 18 | 7 | 26 |
| 18 | 11.0 | 18 | 18 | 2 | 6 |
| 19 | 9.0 | 4.5 | 4.5 | 0 | 1 |
| 20 | 9.5 | 4.5 | 4.5 | 1 | 2 |
| 21 | 10.0 | 4.5 | 4.5 | 3 | 9 |

TABLE 2-continued

| | | substrate concentration (g/100 ml) | | concentration of NANA (mg/ml) | |
|---|---|---|---|---|---|
| Example | pH | GlcNAc | Pyr-Na | after 1 day reaction | after 5 day reaction |
| 22 | 10.5 | 4.5 | 4.5 | 6 | 13 |
| 23 | 11.0 | 4.5 | 4.5 | 1 | 1 |

*concentration of N-acetylneuraminic acid lyase: 1 U/ml
The abbreviations in tables 1 to 2 have the following meanings.
*NANA: N-acetylneuraminic acid
*GlcNAc: N-acetylglucosamine
*Pyr-Na: sodium pyruvate The results of table 1 and table 2 show that according to the method of the present invention, N-acetylglucosamine can be converted into N-acetylneuraminic acid in one step in high yield.

Example 24

* stability of N-acetylneuraminic acid lyase

100 U of N-acetylneuraminic acid lyase, 1.8 g of N-acetylglucosamine and 1.8 g of sodium pyruvate were added to 100 mM phosphate buffer (pH 10.0), the total volume of the solution was adjusted to 10 ml and the mixture was reacted at 35° C. for 16 hours. The remaining activity of N-acetylneuraminic acid lyase after reaction was 100% as determined by dialyzing the reaction mixture against 100 times as much volume of the solution as 50 mM of phosphate buffer (pH 7.5), followed by reacting the lyase with a substrate (N-acetylneuraminic acid) and colorimetrically determining the amount of N-acetylmannosamine formed.

Examples 25 to 43

Stability of N-acetylneuraminic acid lyase was determined in the same conditions as in example 24 except for alteration of concentrations of N-acetylglucosamine and pyruvic acid, a concentration of N-acetylneuraminic acid lyase, reaction time and pH of phosphate buffer respectively.

Comparative Example 2

Stability of N-acetylneuraminic acid lyase was determined in the same conditions as in example 24 except that N-acetylglucosamine and pyruvic acid were not added.

Comparative Examples 3 to 11

Stability of N-acetylneuraminic acid lyase was determined in the same conditions as in comparative example 2 except that the concentration of N-acetylneuraminic acid lyase and pH of phosphate buffer were altered respectively.

The results are demonstrated in table 3 and table 4 as shown below.

TABLE 3

| Ex. or Com. Ex. | pH | substrate concentration (g/100 ml) | | Remaining activity of NANA lyase (%) |
|---|---|---|---|---|
| | | GlcNAc | Pyr-Na | |
| Ex. 24 | 9.0 | 18 | 18 | 100 |
| Ex. 25 | 9.5 | 18 | 18 | 100 |
| Ex. 26 | 10.0 | 18 | 18 | 100 |

TABLE 3-continued

| Ex. or Com. Ex. | pH | substrate concentration (g/100 ml) | | Remaining activity of NANA lyase (%) |
|---|---|---|---|---|
| | | GlcNAc | Pyr-Na | |
| Ex. 27 | 10.5 | 18 | 18 | 80 |
| Ex. 28 | 11.0 | 18 | 18 | 22 |
| Ex. 29 | 9.0 | 4.5 | 4.5 | 100 |
| Ex. 30 | 9.5 | 4.5 | 4.5 | 100 |
| Ex. 31 | 10.0 | 4.5 | 4.5 | 100 |
| Ex. 32 | 10.5 | 4.5 | 4.5 | 80 |
| Ex. 33 | 11.0 | 4.5 | 4.5 | 10 |
| Com. Ex. 2 | 9.0 | 0 | 0 | 100 |
| Com. Ex. 3 | 9.5 | 0 | 0 | 100 |
| Com. Ex. 4 | 10.0 | 0 | 0 | 20 |
| Com. Ex. 5 | 10.5 | 0 | 0 | 0 |
| Com. Ex. 6 | 11.0 | 0 | 0 | 0 |

*concentration of N-acetylneuraminic acid lyase: 10 U/ml

TABLE 4

| Ex. or Com. Ex. | pH | substrate concentration (g/100 ml) | | Remaining activity of NANA lyase (%) |
|---|---|---|---|---|
| | | GlcNAc | Pyr-Na | |
| Ex. 34 | 9.0 | 18 | 18 | 100 |
| Ex. 35 | 9.5 | 18 | 18 | 100 |
| Ex. 36 | 10.0 | 18 | 18 | 97 |
| Ex. 37 | 10.5 | 18 | 18 | 70 |
| Ex. 38 | 11.0 | 18 | 18 | 30 |
| Ex. 39 | 9.0 | 4.5 | 4.5 | 100 |
| Ex. 40 | 9.5 | 4.5 | 4.5 | 100 |
| Ex. 41 | 10.0 | 4.5 | 4.5 | 98 |
| Ex. 42 | 10.5 | 4.5 | 4.5 | 60 |
| Ex. 43 | 11.0 | 4.5 | 4.5 | 8 |
| Com. Ex. 7 | 9.0 | 0 | 0 | 100 |
| Com. Ex. 8 | 9.5 | 0 | 0 | 98 |
| Com. Ex. 9 | 10.0 | 0 | 0 | 15 |
| Com. Ex. 10 | 10.5 | 0 | 0 | 0 |
| Com. Ex. 11 | 11.0 | 0 | 0 | 0 |

*concentration of N-acetylneuraminic acid lyase: 1 U/ml

The results of table 3 and table 4 show that the existence of the substrates, N-acetylglucosamine and pyruvic acid, causes stabilization of unstable N-acetylneuraminic acid lyase in a wider pH range.

We claim:

1. A method for preparing N-acetylneuraminic acid comprising:
   reacting N-acetylglucosamine with pyruvic acid at a pH within the range from about 10 to about 12 in the presence of N-acetylneuraminic acid lyase; and
   recovering N-acetylneuraminic acid.

2. The method as claimed in claim 1, wherein the pH is between about 10 and about 11.

3. The method as claimed in claim 4, wherein the pH is about 10.5.

4. The method as claimed in claim 1, wherein the pH is adjusted by the addition of at least one substance selected from the group consisting of sodium hydroxide, potassium hydroxide, lithium hydroxide, calcium hydroxide, magnesium hydroxide, sodium carbonate, potassium carbonate, sodium bicarbonate, potassium bicarbonate and ammonia.

5. The method as claimed in claim 1, wherein the pH is adjusted by using an alkaline buffer.

6. The method as claimed in claim 5, wherein the alkaline buffer is at least one buffer selected from the group consisting of phosphate buffer, Tris-hydrochloric acid buffer, borate buffer, veronal-hydrochloric acid buffer and diethanolamine-hydrochloric acid buffer.

7. The method as claimed in claim 1, wherein the concentration of N-acetylglucosamine is 1–20 W/V %.

8. The method as claimed in claim 1, wherein the concentration of pyruvic acid is 1–20 W/V %.

9. The method as claimed in claim 1, wherein N-acetylneuraminic acid lyase is used at a concentration of 0.1 to 100 U per 1 ml.

10. The method as claimed in claim 9, wherein the concentration of N-acetylglucosamine is 1–20 W/V %, and the concentration of pyruvic acid is 1–20 W/V %.

11. The method as claimed in claim 9, wherein the concentration of N-acetylglucosamine is 10–20 W/V %, and the concentration of pyruvic acid is 10–20 W/V %.

12. The method as claimed in claim 11, wherein the pH is about 10 to about 11.

13. A method for preparing N-acetylneuraminic acid comprising:

reacting N-acetylglucosamine with pyruvic acid at a pH within the range from about 8 to about 12 in the presence of N-acetylneuraminic acid lyase, but in the absence of epimerase; and recovering N-acetylneuraminic acid.

* * * * *

UNITED STATES PATENT AND TRADEMARK OFFICE
CERTIFICATE OF CORRECTION

PATENT NO. : 5,665,574
DATED : September 9, 1997
INVENTOR(S) : Yoji Tsukada and Yasuhiro Ohta It is certified that error appears in the above-identified patent and that said Letters Patent is hereby corrected as shown below:

On the title page: Item [63] filing date for PCT/JP92/00757, delete "Sep. 12, 1992" and insert --Jun. 12, 1992--.

Signed and Sealed this

Thirty-first Day of March, 1998

Attest:

BRUCE LEHMAN

Attesting Officer

Commissioner of Patents and Trademarks